(12) United States Patent
Bodin et al.

(10) Patent No.: US 8,762,117 B2
(45) Date of Patent: Jun. 24, 2014

(54) METHOD, AN APPARATUS AND COMPUTER PROGRAM PRODUCT FOR SIMULATING DYNAMIC FLUIDS

(75) Inventors: Kenneth Bodin, Umeå (SE); Claude Lacoursière, Umeå (SE); Martin Servin, Umeå (SE)

(73) Assignee: Algoryx Simulation AB, Umeå (SE)

( * ) Notice: Subject to any disclaimer, the term of this patent is extended or adjusted under 35 U.S.C. 154(b) by 371 days.

(21) Appl. No.: 13/320,251

(22) PCT Filed: May 26, 2010

(86) PCT No.: PCT/SE2010/050568
§ 371 (c)(1),
(2), (4) Date: Jan. 30, 2012

(87) PCT Pub. No.: WO2010/140957
PCT Pub. Date: Dec. 9, 2010

(65) Prior Publication Data
US 2012/0123754 A1    May 17, 2012

Related U.S. Application Data

(60) Provisional application No. 61/183,566, filed on Jun. 3, 2009.

(30) Foreign Application Priority Data

Jun. 3, 2009    (SE) ...................................... 0950401

(51) Int. Cl.
*G06G 7/50*  (2006.01)
*G06G 7/57*  (2006.01)
*G01N 1/20*  (2006.01)
*G01N 15/00* (2006.01)
*G06F 17/11* (2006.01)

(52) U.S. Cl.
CPC .. *G06G 7/50* (2013.01); *G06G 7/57* (2013.01); *G01N 1/20* (2013.01); *G01N 15/00* (2013.01); *G06F 17/11* (2013.01)
USPC .......................................................... 703/9

(58) Field of Classification Search
CPC ............ G06G 7/50; G06G 7/57; G06F 17/11; G06F 17/5009; G06F 17/5018; G01N 1/20; G01N 11/00; G01N 13/00; G01N 15/00; G01N 15/06; G01N 15/0826
USPC ............... 703/9, 2; 435/4; 137/487.5; 700/73
See application file for complete search history.

(56) References Cited

U.S. PATENT DOCUMENTS 6,915,245 B1 *   7/2005   Hinton et al. ..................... 703/2
7,099,721 B2 *   8/2006   Dunnill et al. ................... 700/73

(Continued)

OTHER PUBLICATIONS

Hu et al., "An incompressible multi-phase SPH method", Journal of Computational Physics, 2007.*

(Continued)

*Primary Examiner* — Kandasamy Thangavelu
(74) *Attorney, Agent, or Firm* — Morrison & Foerster LLP

(57) ABSTRACT

The invention relates to a method for simulating dynamic fluids comprising a plurality of pseudo particles. The method comprising the steps of: defining a fluid mass density of the pseudo particle masses; defining a mass density constraint such that the mass density on each pseudo particle is constrained to a reference mass density of a real fluid, whereby an instant propagation of density fluctuations through the entire fluid system is enabled; performing constraint stabilization on said mass density constraint using a time stepping function, wherein said time stepping function is arranged to conserve global physical symmetries and is stable for violations of said mass density constraint; solving a linear system of equations for said mass density constraint in order to calculate density constraint forces; calculating new time discrete pseudo particle velocities from previous pseudo particle velocities with addition of velocity increments calculated from said density constraint forces; and calculating new time discrete pseudo particle positions from the previous pseudo particle positions with additions of the position increments calculated from said new pseudo particle velocities. The invention also relates to an apparatus for simulating dynamic fluids and a computer program product for the same.

17 Claims, 7 Drawing Sheets

(56) References Cited

U.S. PATENT DOCUMENTS

| | | | |
|---|---|---|---|
| 2005/0216242 A1 | 9/2005 | Flax et al. | |
| 2005/0257835 A1* | 11/2005 | Midtgard et al. | 137/487.5 |
| 2007/0038424 A1* | 2/2007 | Schirm et al. | 703/9 |
| 2007/0231783 A1* | 10/2007 | Prabhakarpandian et al. | 435/4 |
| 2008/0126045 A1* | 5/2008 | Shan et al. | 703/9 |
| 2008/0154562 A1* | 6/2008 | Blanchette et al. | 703/9 |

OTHER PUBLICATIONS

Hu et al., "A constant-density approach for incompressible multiphase SPH", Journal of Computational Physics, 2009.*

Pozorski et al., "SPH computation of incompressible viscous flows", Journal of theoretical and applied mechanics, 2002.*

International Search Report and Written Opinion received for PCT Patent Application No. PCT/SE2010/050568, mailed on Aug. 26, 2010, 13 pages.

Linde, Mattias, "Parallel Simulation of Particle Fluids", Umea University, Department of Computing Science, Dec. 13, 2007, 43 pages.

Wang et al., "Parallel Implementation of Macro-Scale Pseudo-Particle Simulation for Particle-Fluid Systems", Computers and Chemical Engineering, vol. 29, 2005, pp. 1543-1553.

* cited by examiner

METHOD, AN APPARATUS AND COMPUTER PROGRAM PRODUCT FOR SIMULATING DYNAMIC FLUIDS

CROSS REFERENCE TO RELATED APPLICATIONS

This is a U.S. National Phase patent application of PCT/SE2010/050568, filed May 26, 2010, which claims priority to Swedish Patent Application No. 0950401-0, filed Jun. 3, 2009, and U.S. Provisional Patent Application No. 61/183,566, filed Jun. 3, 2009, each of which is hereby incorporated by reference in the present disclosure in its entirety.

TECHNICAL FIELD

The invention relates in general to the field of fluid simulation, an in particular to a method and an apparatus for simulating dynamic fluids. The invention also relates to a computer program product for the same.

BACKGROUND

Fluid simulation is an essential technology in many areas of technology. For example, it may be used in engineering where dynamic fluid simulation enables testing, optimization and validation of various designs and constructions, or for educational purposes where dynamic fluid simulation enables virtual experiments and exploration based learning. Other examples include virtual reality training simulators (where dynamic fluid simulation enables realistic behavior of ships, vehicles and other machines and devices, as well as load and cargo, or body fluids in surgery training simulators, etc.), environment illustrations in motion pictures (where fluid simulation enable cost effective and spectacular computer generated visual effects of flooding, splashing, explosions and general representation of water and other fluids in containers, floods, lakes and oceans), and contemporary computer games, where interactive simulation of dynamic fluids enriches game play and enables special effects, such as water splashes and explosions.

In a conventional method for pseudo particle based simulation of dynamic fluids, the motion of the simulated fluid is governed by penalty forces that act to preserve the fluid volume and mass density. In addition, the fluid velocity can be corrected by means of a projection of the velocities of a compressible fluid upon a velocity field of a corresponding incompressible fluid. The penalty force method sets severe restriction on the size of the time step of the time discrete computer simulation, since the time step must be small enough to resolve fluctuations of the fluid that propagate through the fluid with the speed of sound of the fluid. The fluid sound speed is often 10-100 times that of other relevant speed scales of the system.

As will become apparent from the description below, conventional penalty force methods are computationally heavy and inefficient in representing dynamic near incompressible fluids. Furthermore, conventional penalty force methods commonly experience severe stabilization problems.

Therefore, conventional methods use a variety of approaches for dealing with the described stability problem. Such methods may comprise a viscosity or damping force being added to the pressure force. The damping of velocities will stabilize the dynamic fluid simulation for larger pressure forces, and thus allow for simulation of more incompressible fluids. However, very large viscosity forces are needed to substantially stabilize these incompressible fluid simulations.

In the limit of very large viscosity forces, these forces will themselves start to contribute instabilities to the simulation, and in addition such large viscosity forces will also give highly unrealistic simulations of even the most ordinary well known fluids that have relatively low internal viscosity.

Thus, the overall effect on the dynamic fluid simulation of a very large viscosity is a slightly more stable simulation, a fluid with a still unrealistic degree of compressibility, and a fluid with too much internal viscosity to be realistic.

SUMMARY

A problem to which the invention relates is the problem of simulating dynamic fluids with an improved computational efficiency.

This problem is addressed by a method for simulating dynamic fluids comprising a plurality of pseudo particles. The method comprising the steps of: defining a fluid mass density of the pseudo particle masses; defining a mass density constraint such that the mass density on each pseudo particle is constrained to a reference mass density of a real fluid, whereby an instant propagation of density fluctuations through the entire fluid system is enabled; performing constraint stabilization on said mass density constraint using a time stepping function, wherein said time stepping function is arranged to conserve global physical symmetries and is stable for violations of said mass density constraint; solving a linear system of equations for said mass density constraint in order to calculate density constraint forces; calculating new time discrete pseudo particle velocities from previous pseudo particle velocities with addition of velocity increments calculated from said density constraint forces; and calculating new time discrete pseudo particle positions from the previous pseudo particle positions with additions of the position increments calculated from said new pseudo particle velocities.

This problem is further addressed by an apparatus for simulating dynamic fluids, comprising a processing unit capable of generating a plurality of pseudo particles and performing a dynamic fluid simulation of said plurality of pseudo particles, said apparatus being adapted to define a fluid mass density of the pseudo particle masses, define a mass density constraint such that the mass density on each pseudo particle is constrained to a reference mass density of a real fluid, whereby an instant propagation of density fluctuations through the entire fluid system is enabled, perform constraint stabilization on said mass density constraint using a time stepping function, wherein said time stepping function is arranged to conserve global physical symmetries and is stable for violations of said mass density constraint, solving a linear system of equations for said mass density constraint, and calculating density constraint forces, calculating new time discrete pseudo particle velocities from previous pseudo particle velocities with addition of velocity increments calculated from said density constraint forces, and calculating new time discrete pseudo particle positions from the previous pseudo particle positions with additions of the position increments calculated from said new pseudo particle velocities.

By having a combined time stepping, constraint stabilization and relaxation method that provides global conservation of physical symmetries of the dynamic simulated incompressible fluid and provides a robust physical and numerical stability under large constraint violations, the method according to the invention provides a substantial improvement in computational efficiency over other known methods.

If the pseudo particles violate a boundary condition of a container, a body floating in the simulated fluid, the method may further comprises the steps of: adding a smoothed boundary density to boundary condition violating pseudo particles; defining a mass density constraint at the boundary such that the mass density of the pseudo particles violating the boundary condition to the reference mass density of the fluid are constrained; and adding this boundary mass density constraint to the mass density constraint.

If the simulated fluid requires a lower degree of viscosity, the method may further comprise the step of: relaxing the mass density constraint such that the mass density constraint dissipates energy upon constraint violation and stabilization in dependence of the mass density constraint being satisfied on the average over time. If, however, the simulated fluid requires a higher degree of viscosity, the method may further comprise the step of: adding a kinematic constraint arranged to constrain the pseudo particle velocities of neighbouring particles.

If a lower degree of fidelity and precision is required, the method may further comprise the step of: solving the linear system of equations by means of sequential solutions to each of the constraint equations, which utilizes the Gauss-Seidel iterative method for solution of linear systems of equations.

If a higher degree of fidelity and precision is required, the method may further comprise the step of: solving the linear system of equations by means of the conjugate gradient iterative method or a direct sparse linear solver method.

Additionally, the method may further comprise the steps of: implementing an interaction constraint, said interaction constraint being entirely consistent with the mass density constraint and with the linear equations, arranged to simulate the interaction between the simulated fluid and a plurality of rigid bodies containing the simulated fluid, floating on top of or inside the simulated fluid; and implementing a rigid body constraint, wherein said rigid body constraint is a non-penetration constraint and a dry friction constraint, arranged to simulate the interaction between rigid bodies, which in effect couples to the simulated fluid through those rigid bodies containing the simulated fluid, floating on top of or inside the simulated fluid. Thus, the rigid body simulation may be made an integral part of the fluid simulation by adding additional equations to the linear systems of equations, thus resulting in an entirely consistent simulation model.

The method may also comprise the step of adding a rigid body inequality constraint, which extends the linear system of equations to a linear complimentarity problem, whereby the step of solving the linear system of equations further comprises an extension to corresponding projected versions far solving linear complimentarity problems.

Further advantageous embodiments of the apparatus and computer program product are set forth in the dependent claims and correspond to the advantageous embodiments already set forth with reference to the previously mentioned method.

BRIEF DESCRIPTION OF THE DRAWINGS

The objects, advantages and effects as well as features of the invention will be more readily understood from the following detailed description of exemplary embodiments of the invention when read together with the accompanying drawings, in which.

DETAILED DESCRIPTION

In order to best illustrate the inventive features of the invention, the invention will be described below in relation to the following example.

If a volume of water is to be resolved at a typical application relevant spatial resolution of 0.01 [m], and a conventional penalty force method is used, the maximum propagation speed of fluctuations in density and volume mediated by the penalty force is one spatial resolution per discrete time step dt, that is, 0.01/dt [m/s]. In order to reproduce incompressibility and in order for the numerical simulation to be stable when simulating, for example, water, this propagation velocity must be comparable or large compared to the real sound speed of water, which is near 1500 [m/s]. Thus, dt must be chosen such that $0.01/dt \gg 1500$ [m/s], and therefore the time step must satisfy $dt \ll 6.67 \cdot 10e\text{-}6$ [s]. The typically used time step size in application areas described above correspond to the image generation frame rates of 30-60 [Hz], and thus a time step of dt within the range of 0.0167-0.033 [s]. This time step size is 4-5 orders of magnitude too large to represent stable and incompressible fluids when utilizing conventional penalty force methods. A corresponding reduction of the time step size in the application will increase the computational cost 4-5 orders of magnitude and a conclusion is therefore that conventional penalty force methods are computationally heavy and inefficient in representing dynamic near incompressible fluids.

Figure 1:
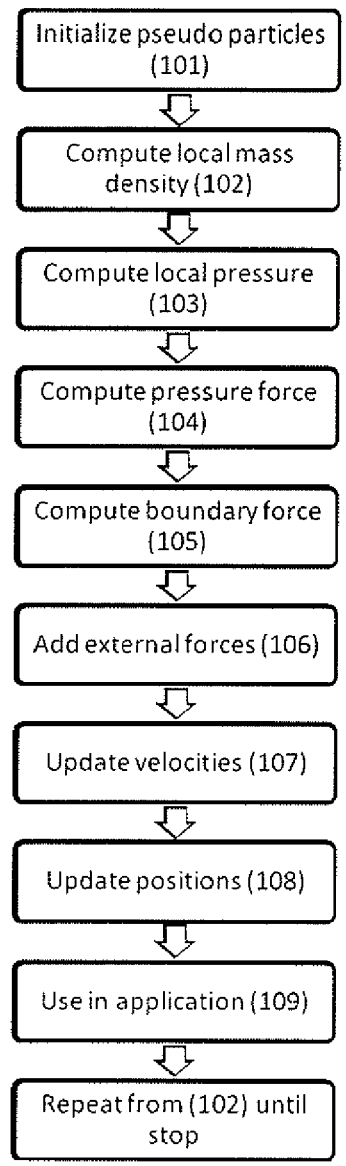
FIG. 1 shows a flowchart of a method for simulating dynamic fluids according to prior art.

In FIG. 1, a conventional penalty based method for dynamic fluid simulation is shown. The conventional method comprises a spatial discretization of the fluid into pseudo particles in step 101. The method further comprises the computing of the fluid mass density as a weighted average over pseudo particle masses in step 102. A constitutive law is then used to compute the local pressure in step 103, whereby the pressure is used to compute pressure forces acting on the particles in step 104. External forces are added to the total force in step 105. Boundary forces are also added to the total force in step 106. The pressure force is then used to compute updated time discrete pseudo particle velocities in step 107 and the updated pseudo particle velocities are used to compute new pseudo particle positions in step 108. The time step is completed and the new pseudo particle positions and other variables can be used for visual or other representation in an application in step 109. Thereafter, the method is repeated from step 102 until the dynamic fluid simulation is stopped by, for example, the user or the application.

However, a significant drawback of the conventional penalty force methods as described above is that: given a fixed time step of convenient size for the application, the magnitude of the pressure force computed in step 103 must be adapted so as to make the simulation stable. If the pressure force is too large relative to the time step, the pseudo particles positions in step 108 will be such that pseudo particles overshoots and a too large or too small density is generated in step 102 instead. This, in turn, will results in an even greater pressure in step 103 and forces of even larger magnitude will be generated in step 104. Thus, very large velocities will be generated in step 107 and lead to a further increased overshoot in pseudo particle positions in step 108, etc. In effect, in case of this and other conventional methods, the pseudo particle system will thus become unstable and explode, and therefore will be useless for the application in step 109.

According to the invention, a method of simulating dynamic fluids is disclosed comprising a set of pseudo particles used to represent physical quantities of the fluid. In said method, a fluid density is calculated from a weighted average over the pseudo particles, and a density constraint on the fluid density constraining it to be incompressible with the reference density of a real physical fluid that is modeled. The constraint stabilization forces of the density constraint will govern the dynamics of the pseudo particles and the simulated fluid. In further detail, the method comprises a combined time stepping, constraint stabilization and relaxation method that provides global conservation of physical symmetries of the simulated fluid, and therefore robust physical and numerical stability under large and extreme constraint violations. The method therefore provides a substantial improvement in computational efficiency over other known methods. Advantageous exemplary embodiments of the invention are described in more detail below with reference to FIGS. 2-7.

Figure 2:
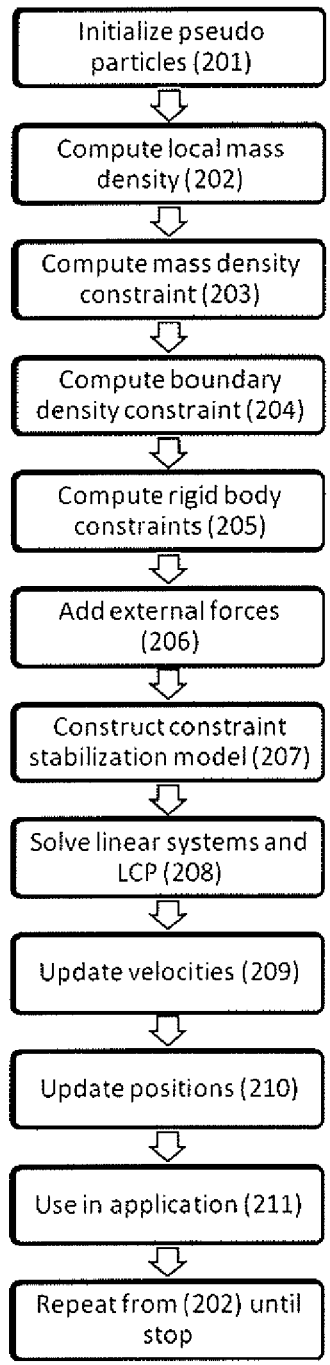
FIG. 2 shows a flowchart of a method for simulating dynamic fluids according to an exemplary embodiment of the present invention.

FIG. 2 schematically illustrates an exemplary embodiment of the method according to the invention, where mass density constraints are used for simulating a dynamic near incompressible fluid. The dynamic near incompressible fluid is modeled by a set of pseudo particles, where each particle has a mass, a position, and a velocity.

Referring to FIG. 2, pseudo particles are initially arranged so that they fill out a volume representative for the real fluid to be modeled, with positions and velocities so that they accurately represent the mass density distribution and velocity distribution of this real fluid (step 201). The method comprises the computation of the mass density at each pseudo particle by means of a weighted sum over the masses of neighboring pseudo particles (step 202). The method further comprise that a constraint is defined that constrains the pseudo particle density to the reference density of the real fluid that is modeled (step 203). Furthermore, for pseudo particles next to a container boundary or other interacting body, a boundary constraint is defined that constrains the mass density at the boundary to the reference density of a real fluid (step 204). For rigid bodies interacting with each other and only indirectly with the fluid boundary, the method devises that non-penetration constraints, friction constraints or other constraints in the degrees of freedom of these bodies are added to the fluid-fluid constraints and the fluid-boundary constraints (step 205).

The method further devises that all other external forces acting on fluid or other dynamic bodies of the system are summed up and added to their respective total forces (step 206). The devised discrete equations of motion of the system are collected, incorporating the summarized external forces, as well as all constraints into a constraint stabilization model (step 207), resulting in a system of linear equations and in general a linear complimentarity system, that is solved for the constraint forces using a choice of either iterative or direct sparse methods or a hybrid combination thereof (step 208). The time discrete pseudo particle velocities and all other dynamic body velocities are updated by application of the computed constraint forces, as well as other external forces over the discrete time step (step 209). The time discrete positions of the pseudo particles and all other dynamic bodies are updated using the updated velocities (step 210). Positions, velocities and other quantities and variables of the pseudo particles and all other dynamic bodies are used in the application for visual presentation or other means (step 211). The simulation procedure may be repeated from (step 202) until stopped by the application or the user.

An exemplary embodiment of the method above are described more in detail below, wherein the method prescribes that a real world fluid of total volume V, total mass M, density $\rho_0 = M/V$ is simulated using N pseudo particles, each with mass $m_i$, where i is a particle index.

The local mass density of particle j is represented by, $$\rho_j = \sum_i m_i K(r_{ij})$$

The sum over i runs over all N particles including j. $K(r_{ij})$ is a smoothing function that distributes the mass $m_i$ in a particle volume consisting of a sphere with radius h, where h is referred to as the smoothing length. The smoothing function is thus positive and finite for particle distance, $r_{ij}$, smaller than h and zero outside h. Furthermore, the curvature of the smoothing function falls to zero at h, and the smoothing function is normalized inside the volume defined by h. In describing the invention we choose the following smoothing function, $$K(r_{ij}) = \frac{315}{64\pi h^9}(h^2 - r_{ij}^2)^3$$

This expression is valid for $0 < r_{ij} < h$ whereas the smoothing function is set to zero for $r_{ij} > h$. The invention prescribes that a density conservation constraint, $g_i$, is constructed to measure the violation in the local mass density $\rho_i$, at each particle i, from the reference density, $\rho_0$, of the real fluid, $$g_i = \rho_i - \rho_0$$

The corresponding kinematic constraint, $\dot{g}_i$, measures the speed of the constraint violation, and can be computed from the time derivative of the definition of $g_i$. In general, the kinematic constraint vector, g, for all particles can be computed from $$\dot{g} = \frac{dg}{dt} = \frac{\partial g}{\partial r}\frac{dr}{dt} = Gv$$

where $G = \frac{\partial g}{\partial r}$ is the Jacobian matrix of the constraint vector g, and $v$ is the vector of all particle velocities. Using the definition of $g_i$, and the definition of $\rho_i$ the kinematic constraint for particle i takes the form, $$\dot{g}_i = \sum_j \frac{dK(r_{ij})}{dr_{ij}} \hat{r}_{ij} \cdot v_{ij}$$

where $\hat{r}_{ij}$ is the normalized unit vector pointing from the center of particle i to the center of particle j, and $v_{ij}$ is the corresponding velocity vector. From this result for $\dot{g}_i$ and the definition of the Jacobian matrix G above, the matrix components can be computed, $$G_{ij} = -m_j \frac{dK(r_{ik})}{dr_{ij}} \hat{r}_{ij}^T$$

$$G_{ii} = \sum_k m_k \frac{dK(r_{ik})}{dr_{ik}} \hat{r}_{ik}^T$$

The Lagrange multipliers, λ, of the constraint g, correspond to constraint forces f, and are related through the Jacobian matrix as, $f=G^T\lambda$, and can be computed from, $$f_i = \sum_j (m_i \lambda_i + m_j \lambda_j) \frac{dK(r_{ij})}{dr_{ij}} \hat{r}_{ij}$$

The Lagrange multipliers, λ, in turn are computed from a variational time discrete framework of the form, $$(G_k M^{-1} G_k^T + \Sigma)\lambda = -\frac{4}{\Delta t}\Gamma g_k + \Gamma G_k v_k - G_k M^{-1}(M v_k + \Delta t f_k^{ext})$$

This equation has a general form Ax=b of a sparse linear system of equations and can be readily solved for the unknown Lagrange multipliers λ. The index k, corresponds to the discrete time $t_k=t_o+k\Delta t$, where $t_o$ is the starting time of the simulation. M is the mass matrix containing all particle masses $m_i$, $f_k^{ext}$ accounts for all external forces, such as gravity. Here, Σ is a regularization term that removes inertia from the constraints and r is a stabilization and damping term that determines the time for constraint stabilization. They have the following definitions on diagonal matrix form, $$\Sigma = \frac{4}{\Delta t^2} \text{diag}\left(\frac{\epsilon_1}{1+4\frac{\tau_1}{\Delta t}}, \frac{\epsilon_2}{1+4\frac{\tau_2}{\Delta t}}, \ldots, \frac{\epsilon_{m_k}}{1+4\frac{\tau_{m_k}}{\Delta t}}\right)$$

$$\Gamma = \text{diag}\left(\frac{\gamma_1}{1+4\frac{\tau_1}{\Delta t}}, \frac{\gamma_2}{1+4\frac{\tau_2}{\Delta t}}, \ldots, \frac{\gamma_{m_k}}{1+4\frac{\tau_{m_k}}{\Delta t}}\right)$$

$\gamma_1 \ldots \gamma_{m_k}$ here refer to a magnitude of the damping for each constraint. In most cases we set it to unity, which corresponds to critical damping. $\tau_1 \ldots \tau_{m_k}$ model the relaxation time of each constraint, so that e.g. $\tau=3\Delta t$ means that the constraint is relaxed in three time steps. $\epsilon_1 \ldots \epsilon_{m_k}$ set the magnitude of the regularization of each constraint.

The linear equation that we have introduced can be solved using standard methods from the literature, such as linear iterative methods of type Jacobi, Gauss-Seidel and SOR(w), or Krylov subspace iterative methods such as the preconditioned conjugate gradient method, multi-grid methods, or direct sparse methods, or any other numerical or mathematical method for solving sparse linear systems. The resulting solution, the Lagrange multipliers, are used to compute constraint forces, and the velocities and positions of the system are then the equations of motion are integrated in discrete time using a standard Leapfrog-Verlet scheme according to, $$v_{k+1} = v_k + \Delta t M^{-1} F_k$$

$$r_{k+1} = r_k + \Delta t v_{k+1}$$

where F is the total force, including all constraint forces and external forces.

In the embodiment of the invention, boundary conditions are accounted by means of a boundary field that adds a contribution $\rho_b = m_b K(r_{ib})$ to the density of particle i, within the smoothing distance $h_b$ of the boundary, where $m_b$ is the fluid mass contributed by the boundary and $r_{ib}$ is the distance between particle i and the boundary. This results in a contribution to the Jacobian, and correspondingly a Lagrange multiplier boundary constraint force to be solved for in the linear system, adding a boundary force to the total force in the time discrete equations of motion. This boundary force results in non-penetration of the fluid and the boundary, and the net effect of this force also results in buoyancy forces between the boundary body and the fluid.

Furthermore, according to the invention, the fluid simulation method is efficiently integrated with simulations of rigid bodies. Such bodies interact with the fluid through the above described boundary field. In addition, rigid bodies interact with each other through non-penetration constraint forces and friction forces, in effect from non-penetration constraints and friction constraints. These constraints are inequality constraints and add to the overall Jacobian matrix included in the linear system of equations to be solved for the Lagrange multipliers, extending this linear system to a linear complimentarity system (LCP), which in turn also can be solved utilizing standard methods from the literature, such as projected linear iterative methods of type projected Jacobi, projected Gauss-Seidel and projected SOR(w), or projected Krylov subspace iterative methods such as the preconditioned projected conjugate gradient method, projected multi-grid methods, or direct sparse methods, or any other numerical or mathematical method for solving sparse linear systems.

Figure 3A:
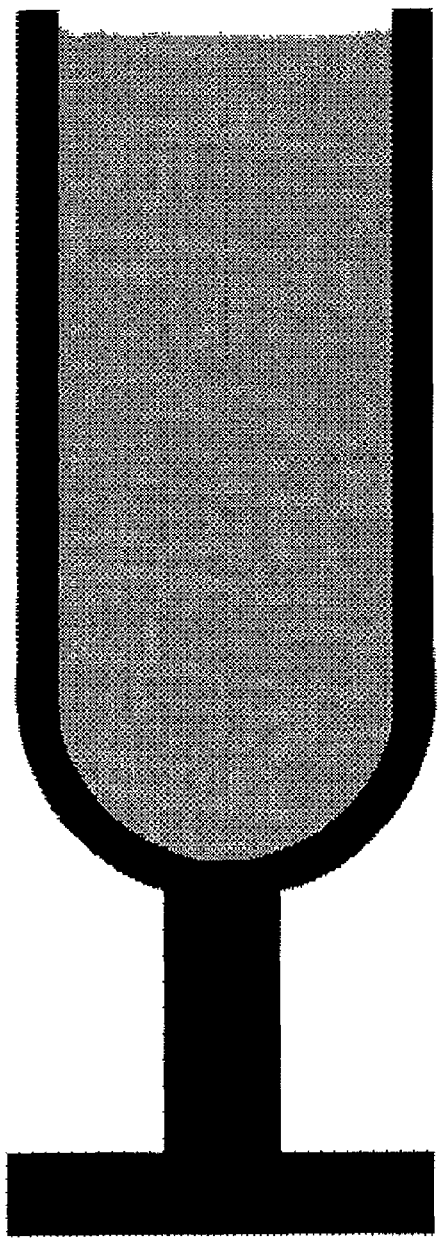
FIG. 3A illustrates the result of a dynamic fluid simulation according to an exemplary embodiment of the present invention.
Figure 3B:
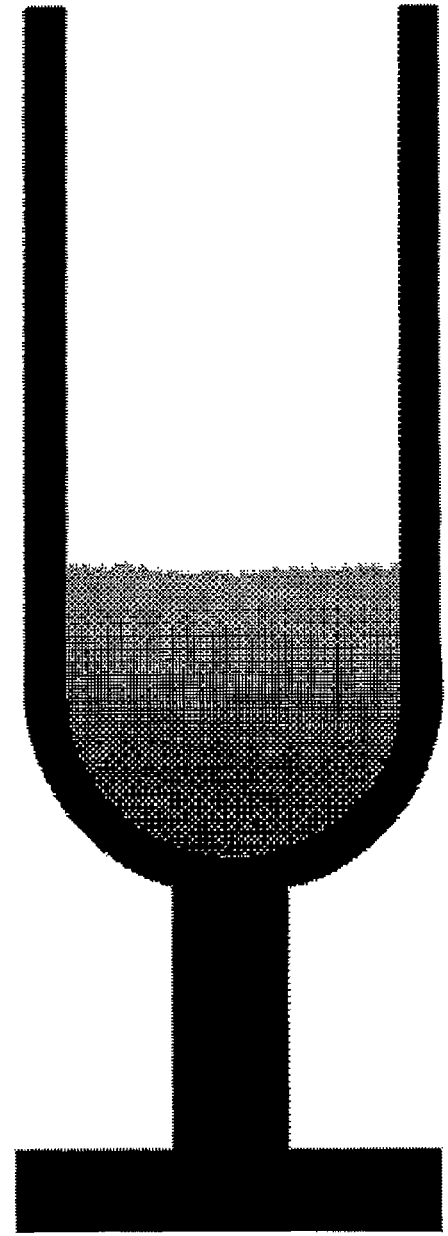
FIG. 3B illustrates the result of a dynamic fluid simulation according to prior art.

FIGS. 3A-B illustrate an exemplary embodiment of the invention wherein the constraint fluid model shown in FIG. 3A is compared with a conventional simulation method shown in FIG. 3B for a fluid in a container subject to a gravitational field. From FIG. 3B, it is clear that the conventional method results in a serious compression of the fluid density that increases with the depth of fluid.

In FIGS. 3A-B, the inventive method and constraint fluid model (FIG. 3A) is compared with a conventional method (FIG. 3B) for a volume of water in a container subject to a gravitational field simulated with a given size of the time step, $\Delta t=1/100$ [s]. Here, the invented method results in a realistic and nearly perfectly incompressible model of water with near constant density throughout the fluid volume, whereas the conventional method which has been driven to the limits of its stability at this given time step, which has resulted in a unrealistic 300% overall compression, and may reach as much as 800% compression at the bottom of the container.

Figure 4:
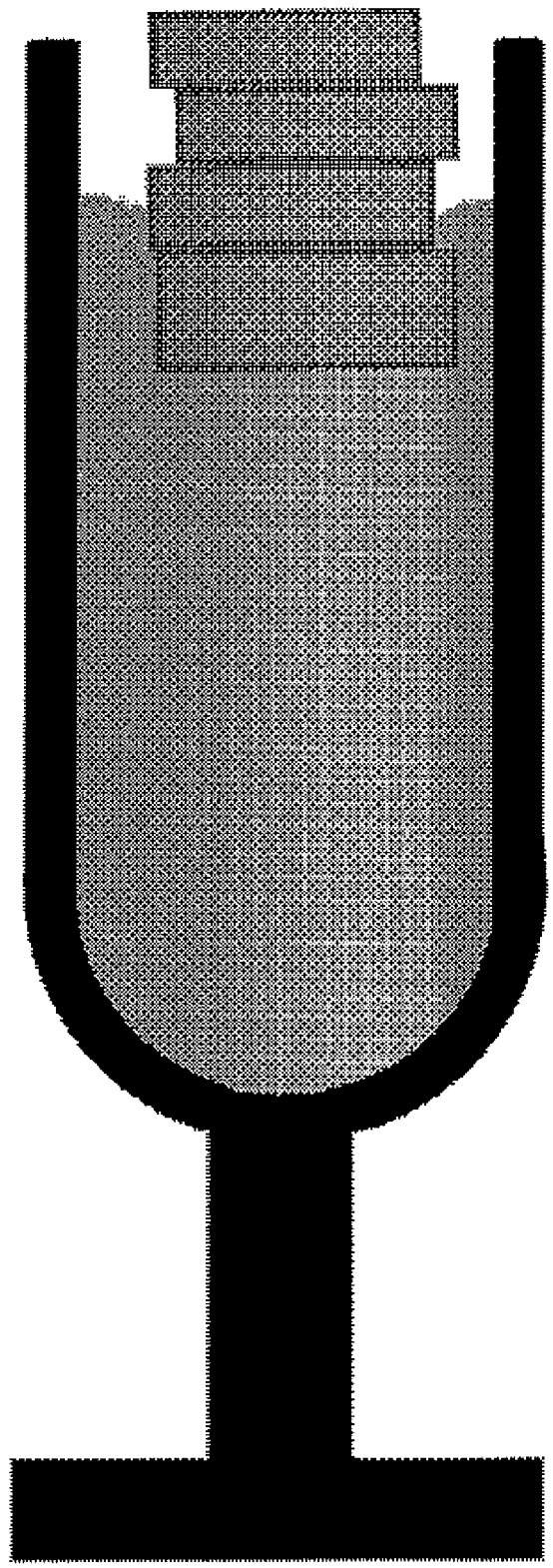
FIG. 4 illustrates a result of a dynamic fluid simulation integrated with rigid body simulation.

FIG. 4 illustrates an exemplary embodiment of the invention where the dynamic fluid simulation is consistently integrated with a rigid body simulation for a rigid body stack floating in the simulated fluid. This also illustrates the action of buoyancy forces and the principle of Archimedes, and may, for example, be used in science education or similar.

Figure 5:
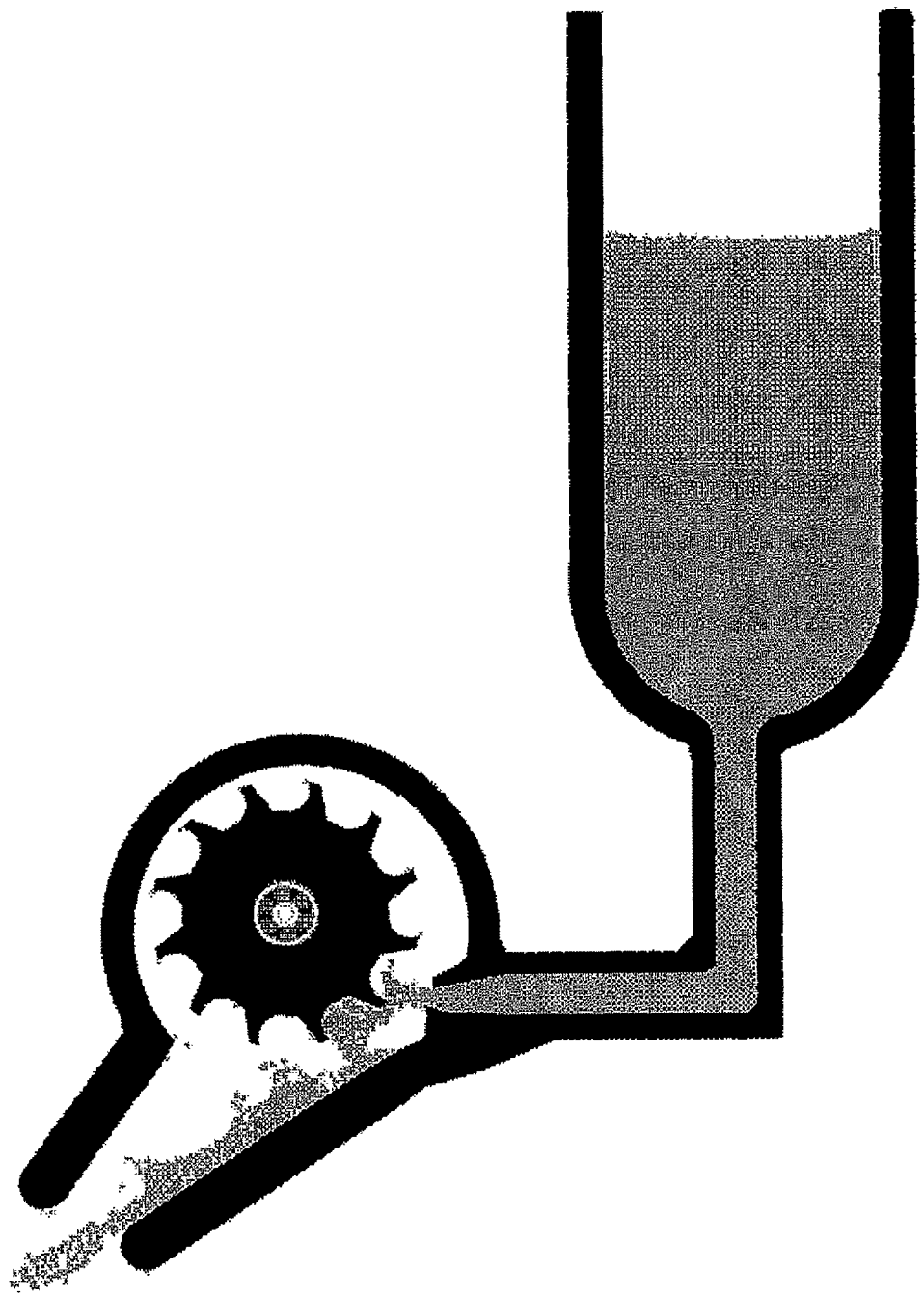
FIG. 5 illustrates a result of a dynamic fluid simulation simulating an impulse driven hydro power plant with a Pelton turbine wheel.

FIG. 5 illustrates an exemplary embodiment of the invention in an engineering example, namely for simulating an impulse driven hydro power plant with a simplified Pelton turbine wheel wheel.

Figure 6:
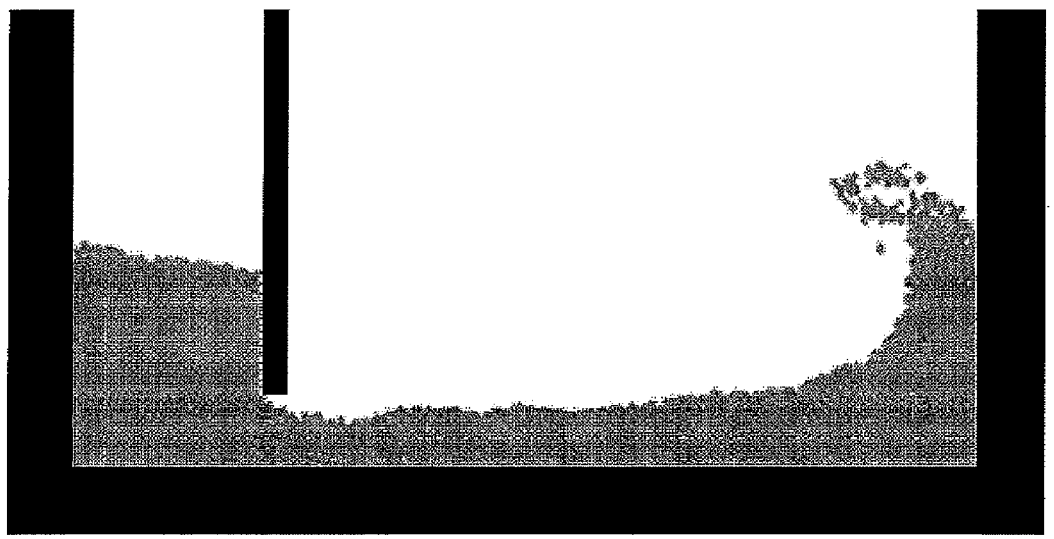
FIG. 6 illustrates a result of a dynamic fluid simulation simulating a dam break.

FIG. 6 illustrates an exemplary embodiment of the invention when simulating a dam break. The dam break example is benchmark problem often used in contemporary scientific and engineering literature. This also illustrates an exemplary embodiment of the invention for its application in computer graphics applications and motion picture visual effects for simulating flooding waves.

Furthermore, from the exemplified and illustrated embodiments of the invention it is clear that the invention may also apply to: interactive simulation of dynamic fluids enriching computer game play and special effects, such as fluid driven machines, water splashes and explosions; motion pictures where fluid simulation enable cost effective and spectacular computer generated visual effects of flooding, splashing, explosions and general representation of water and other fluids in containers, floods, lakes and oceans; engineering where fluid simulation enables testing, optimization and validation of design and constructions; in educational software where fluid simulation enables virtual experiments and exploration based learning; in virtual reality training simulators where fluid simulation enables realistic behavior of ships, vehicles and other machines and devices, as well as load and cargo, and body fluids in surgery training simulators.

Figure 7:
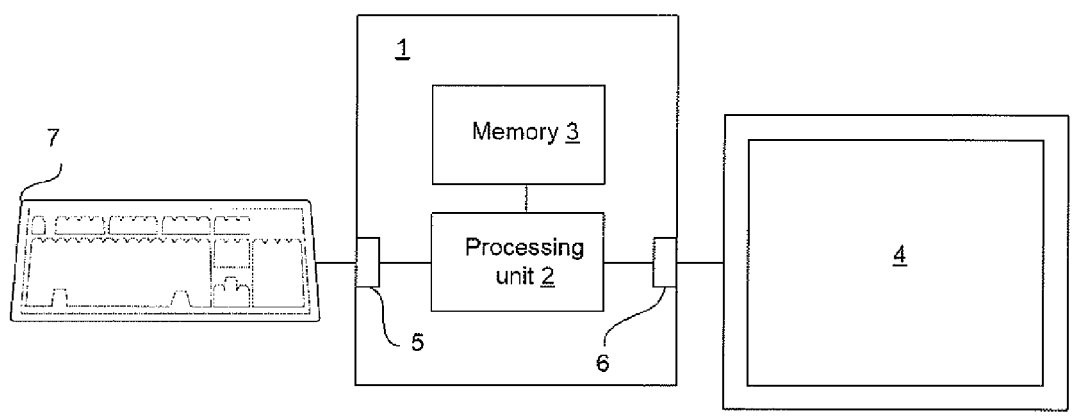
FIG. 7 illustrates an example of an apparatus according to the invention.

FIG. 7 illustrates an example of an apparatus 1 according to the invention. The apparatus 1 may comprises a processing unit 2, a first external interface 5 and a second external interface 6. The processing unit 2 may be connected, through the external interface 5, to a user input device 7. The processing unit 2 may be arranged to receive information from the user input device 7 indicating that a user of an apparatus 1 wants to perform a dynamic fluid simulation according to the invention. The processing unit 2 may further be arranged to receive information through the external interface 5 to be used in the dynamic fluid simulation according to the invention. The user input device 7 may be, for example, a keyboard, a mouse, touch screen or similar, or a communication unit for remotely receiving the user information, such as, for example, over the internet.

As a user of the apparatus 1 indicates to the apparatus 1, through the user input device 7, that a dynamic fluid simulation according to the invention should be performed, the method may be executed by the apparatus by running computer code instructing the apparatus to perform the method steps described above. In general terms, it should thus be understood that the invention typically is implemented as a computer program which, when run on a computer or any other device comprising a processing unit, such as a microprocessor, causes the apparatus 1 to perform the method steps.

It should also be noted that the invention may be implemented in any of a variety of software configurations, or on any of a variety of computing platforms. For example, the dynamic fluid simulation can be run as a single application on the same processor or processing unit as the main application, or on another processor such as a different core of a multi-core processor. It may also, for example, be run on a different computer processing unit (CPU) on a multi-CPU machine, on a graphics processing unit (GPU) or on a computer processing unit (CPU). Furthermore, it may also be run on a networked processing unit, or any other processor capable of the numerical computations devised for the method.

Also, the invention may be implemented on a variety of processing hardware and computing platforms, in a variety of software configurations. For example, the invention may be implemented in a stand-alone computer program product, in a program component product loaded by other computer programs, or in a software development kit or software library integrated with other computer program products. The computer program product embodying the invention can be run on a single processor, on one or several instances on a multiprocessor or multi-core computing platform, on one or several instances on a graphics processing unit of a graphics card, or on one or several instances on a dedicated physics processing unit, on a different computer with networked communication or on a grid or cloud of computing platforms, on a mobile computing platform or any other instance of a computing platform.

The processing unit 2 may also comprise storage means or a memory unit for storing the computer program and processing means or a processing unit, such as a microprocessor, for executing the computer program. The storage means may also be readable storage medium 3 separated from, but connected to the control unit 34. Thus, the processing unit 2 has computational and storage capabilities, which may be provided as one physical unit, or alternatively as a plurality of logically interconnected units.

The processing unit 2 may be arranged to output the results of the method according to invention through the first and/or the second external interface 6. The second external interface 6 may, for example, be connectable to a display unit 4 arranged to demonstrate the results of the method according to the invention in a graphical user interface (GUI) to the user of the apparatus 1.

In short the invention may be described as implemented in order to overcome the generic problems of conventional simulation methods for dynamic fluids utilizing penalty based pressure forces. The invention describes several techniques where the density and volume fluctuations are modeled to propagate through the system at very high speeds, almost at infinite speed. Thus, the corresponding pressure forces also may propagate instantly through the entire system at each time step.

According to one aspect of the invention, a local density conservation constraint resulting in local constraint forces with instant and global connectivity is described.

According to another aspect of the invention, the dynamics of the density conservation constraint is devised so that: small fluctuations in the mass density constraint are made consistent with physical density fluctuations of a real fluid; dissipation of energy due to constraint violation and constraint stabilization is made consistent with viscous energy dissipation of a real fluid.

According to yet another aspect of the invention, a method for solving the linear system of equations resulting from the time discrete model of the density conservation constraints is provided.

According to a further aspect of the invention, a method for simulating a dynamic fluid in a container and subject to boundary conditions and a gravitational field is provided.

According to a further embodiment of the invention, a method for extending the fluid simulation with simulation of a plurality of dynamic rigid bodies containing the fluid, floating on or in the fluid is provided. Further aspects of the invention are exemplified for: engineering types of applications; educational and learning applications; training simulators; motion picture visual effects; computer games. These embodiments apply both in two and three spatial dimension.

The description above is of the best mode presently contemplated for practising the present invention. The description is not intended to be taken in a limiting sense, but is made merely for the purpose of describing the general principles of the invention. The scope of the present invention should only be ascertained with reference to the issued claims.

The invention claimed is:

1. A computer implemented method for simulating dynamic fluids comprising a plurality of pseudo particles, the method comprising the steps of:
defining, using a computer, a mass density of the pseudo particle masses;
defining, using the computer, a mass density constraint such that the mass density on each pseudo particle is constrained to a reference mass density of a real fluid, whereby an instant propagation of density fluctuations through the entire fluid system is enabled;

performing, using the computer, constraint stabilization on said mass density constraint using a time stepping function, wherein said time stepping function is arranged to conserve physical symmetries globally and is stable for violations of said mass density constraint;

solving, using the computer, a linear system of equations for said mass density constraint in order to calculate density constraint forces;

calculating, using the computer, new time discrete pseudo particle velocities from previous pseudo particle velocities with addition of velocity increments calculated from said density constraint forces; and calculating, using the computer, new time discrete pseudo particle positions from the previous pseudo particle positions with additions of position increments calculated from said new pseudo particle velocities.

2. A method according to claim 1, wherein if the pseudo particles violate a boundary condition of a container, a body floating in the simulated fluid, the method further comprises the steps of:

adding a smoothed boundary density to boundary condition violating pseudo particles;

defining a mass density constraint at the boundary such that the mass density of the pseudo particles violating the boundary condition to the reference mass density of the fluid are constrained; and adding this boundary mass density constraint to the mass density constraint.

3. A method according to claim 1, wherein if the simulated fluid requires a lower degree of viscosity, the method further comprises the step of:

relaxing the mass density constraint such that the mass density constraint dissipates energy upon constraint violation and stabilization in dependence of the mass density constraint being satisfied on the average over time.

4. A method according to claim 1, wherein if the simulated fluid requires a higher degree of viscosity, the method further comprises the step of:

adding a kinematic constraint arranged to constrain the pseudo particle velocities of neighbouring particles.

5. A method according to claim 1, wherein if a lower degree of fidelity and precision is required, the method further comprises the step of:

solving the linear system of equations by means of sequential solutions to each of the constraint equations, which utilizes the Gauss-Seidel iterative method for solution of linear systems of equations.

6. A method according to claim 1, wherein if a higher degree of fidelity and precision is required, the method further comprises the step of:

solving the linear system of equations by means of the conjugate gradient iterative method or a direct sparse linear solver method.

7. A method according to claim 1, further comprising the steps of:

implementing an interaction constraint, said interaction constraint being entirely consistent with the mass density constraint and with the linear equations, arranged to simulate the interaction between the simulated fluid and a plurality of rigid bodies containing the simulated fluid, floating on top of or inside the simulated fluid or similar; and implementing a rigid body constraint, wherein said rigid body constraint is a non-penetration constraint and a dry friction constraint, arranged to simulate the interaction between rigid bodies, which in effect couples to the simulated fluid through those rigid bodies containing the simulated fluid, floating on top of or inside the simulated fluid.

8. A method according to claim 1, further comprising the step of:

adding a rigid body inequality constraint, which extends the linear system of equations to a linear complimentarity problem, whereby the step of solving the linear system of equations further comprises an extension to corresponding projected versions for solving linear complimentarity problems.

9. An apparatus for simulating dynamic fluids, comprising a processing unit capable of generating a plurality of pseudo particles and performing a dynamic fluid simulation on said plurality of pseudo particles, said apparatus being adapted to define a fluid mass density of the pseudo particle masses, define a mass density constraint such that the mass density on each pseudo particle is constrained to a reference mass density of a real fluid, whereby an instant propagation of density fluctuations through the entire fluid system is enabled, perform constraint stabilization on said mass density constraint using a time stepping function, wherein said time stepping function is arranged to conserve global physical symmetries and is stable for violations of said mass density constraint, solving a linear system of equations for said mass density constraint, and calculating density constraint forces, calculating new time discrete pseudo particle velocities from previous pseudo particle velocities with addition of velocity increments calculated from said density constraint forces, and calculating new time discrete pseudo particle positions from the previous pseudo particle positions with additions of the position increments calculated from said new pseudo particle velocities.

10. An apparatus according to claim 9, wherein if the pseudo particles violate a boundary condition of a container, a body floating in the simulated fluid, the apparatus is arranged to add a smoothed boundary density to boundary condition violating pseudo particles, define a mass density constraint at the boundary such that the mass density of the pseudo particles violating the boundary condition to the reference mass density of the fluid are constrained, and add said boundary mass density constraint to the mass density constraint.

11. An apparatus according to claim 9, wherein if the simulated fluid requires a lower degree of viscosity, the apparatus is arranged to relax the mass density constraint such that the mass density constraint dissipates energy upon constraint violation and stabilization in dependence of the mass density constraint being satisfied on the average over time.

12. An apparatus according to claim 9, wherein if the simulated fluid requires a higher degree of viscosity, the apparatus is arranged to add a kinematic constraint arranged to constrain the pseudo particle velocities of neighbouring particles.

13. An apparatus according to claim 9, wherein if a lower degree of fidelity and precision is required, the apparatus is arranged to solve the linear system of equations by means of sequential solutions to each of the constraint equations, which utilizes the Gauss-Seidel iterative method for solution of linear systems of equations.

14. An apparatus according to claim 9, wherein if a higher degree of fidelity and precision is required, the apparatus is arranged to solve the linear system of equations by means of the conjugate gradient iterative method or a direct sparse linear solver method.

15. An apparatus according to claim 9, further being arranged to implement an interaction constraint, said interaction constraint being entirely consistent with the mass density constraint and with the linear equations, arranged to simulate the interaction between the simulated fluid and a plurality of rigid bodies containing the simulated fluid, floating on top of or inside the simulated fluid, and implement a rigid body constraint, wherein said rigid body constraint is a non-penetration constraint and a dry friction constraint, arranged to simulate the interaction between rigid bodies, which in effect couples to the simulated fluid through those rigid bodies containing the simulated fluid, floating on top of or inside the simulated fluid or similar.

16. An apparatus according to claim 9, further being arranged to add a rigid body inequality constraint, which extends the linear system of equations to a linear complimentarity problem, whereby the step of solving the linear system of equations further comprises an extension to corresponding projected versions for solving linear complimentarity problems.

17. A non-transitory computer readable medium storing computer executable instructions for use in an apparatus for simulating dynamic fluids comprising a plurality of pseudo particles, which when run in a processing unit in the apparatus causes said processing unit to perform the steps of:

defining a fluid mass density of the pseudo particle masses;

defining a mass density constraint such that the mass density on each pseudo particle is constrained to a reference mass density of a real fluid, whereby an instant propagation of density fluctuations through the entire fluid system is enabled;

performing constraint stabilization on said mass density constraint using a time stepping function, wherein said time stepping function is arranged to conserve global physical symmetries and is stable for violations of said mass density constraint;

solving a linear system of equations for said mass density constraint, and calculating density constraint forces;

calculating new time discrete pseudo particle velocities from previous pseudo particle velocities with addition of velocity increments calculated from the density constraint forces; and calculating new time discrete pseudo particle positions from the previous pseudo particle positions with additions of the position increments calculated from the new pseudo particle velocities.

* * * * *